US008229567B2

(12) United States Patent  
Phillips et al.

(10) Patent No.: US 8,229,567 B2  
(45) Date of Patent: Jul. 24, 2012

(54) CONCENTRIC PRIMARY COILS FOR INDUCTIVELY CHARGING AN IMPLANTABLE MEDICAL DEVICE, EXTERNAL POWER SOURCE AND METHOD

(75) Inventors: William C. Phillips, Brooklyn Park, MN (US); David P. Olson, Minnetrista, MN (US); Erik G. Widman, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 902 days.

(21) Appl. No.: 12/112,760

(22) Filed: Apr. 30, 2008

(65) Prior Publication Data

US 2009/0276016 A1 Nov. 5, 2009

(51) Int. Cl.  
*A61N 1/08* (2006.01)
(52) U.S. Cl. .......................................... 607/60
(58) Field of Classification Search ............... 607/60, 607/61, 33  
See application file for complete search history.

(56) References Cited

U.S. PATENT DOCUMENTS

| | | | |
|---|---|---|---|
| 6,047,214 | A | 4/2000 | Mueller et al. |
| 6,212,430 | B1 | 4/2001 | Kung |
| 6,345,203 | B1 | 2/2002 | Mueller et al. |
| 6,366,817 | B1 | 4/2002 | Kung |
| 6,400,991 | B1 | 6/2002 | Kung |
| 6,463,329 | B1 | 10/2002 | Goedeke |
| 2002/0087204 | A1* | 7/2002 | Kung et al. ............ 607/61 |
| 2003/0078634 | A1 | 4/2003 | Schulman et al. |
| 2004/0098068 | A1 | 5/2004 | Carbunaru et al. |
| 2004/0212344 | A1 | 10/2004 | Tamura et al. |
| 2005/0075694 | A1 | 4/2005 | Schmeling et al. |
| 2005/0088357 | A1* | 4/2005 | Hess et al. ............ 343/788 |
| 2005/0131495 | A1 | 6/2005 | Parramon et al. |
| 2005/0137644 | A1 | 6/2005 | Bojeva et al. |
| 2006/0129056 | A1* | 6/2006 | Leuthardt et al. ............ 600/544 |
| 2008/0172109 | A1* | 7/2008 | Rahman et al. ............ 607/60 |

FOREIGN PATENT DOCUMENTS

| | | |
|---|---|---|
| WO | WO 00/66221 | 11/2000 |
| WO | WO 01/74447 A2 | 10/2001 |
| WO | WO 02/053226 A2 | 7/2002 |
| WO | WO 03/039652 A2 | 5/2003 |
| WO | WO 2004/038888 A2 | 5/2004 |

OTHER PUBLICATIONS http://www.merriam-webster.com/dictionary/concentric , Jun. 1, 2011.*  
International Search Report for PCT/US2009/030985.

* cited by examiner

*Primary Examiner* — Carl H Layno  
*Assistant Examiner* — Paula J Stice  
(74) *Attorney, Agent, or Firm* — IPLM Group, P.A.

(57) ABSTRACT

An external antenna with a plurality of concentric primary coils recharges an implantable medical device with a secondary coil when the primary coils are placed in proximity of the secondary coil. Selection circuitry determines which of the plurality of concentric primary coils has the most efficient coupling with the secondary coil and drive circuitry drives the selected primary coil with an oscillating current. During a recharge session, selection circuitry periodically checks at least some of the primary coils to determine whether the primary coil with the most efficient connection has changed. An antenna housing may hold the primary coils in a rigid planar relationship with each other or the primary coils may shift with respect to each other, forming a cup-shape around a bulge in the skin created by the implantable medical device.

15 Claims, 9 Drawing Sheets

CONCENTRIC PRIMARY COILS FOR INDUCTIVELY CHARGING AN IMPLANTABLE MEDICAL DEVICE, EXTERNAL POWER SOURCE AND METHOD

FIELD

The present invention is related to implantable medical devices and, in particular, implantable medical devices having a rechargeable power source.

BACKGROUND

Implantable medical devices for producing a therapeutic result in a patient are well known. Examples of such implantable medical devices include, but are not limited to, implantable drug infusion pumps, implantable neurostimulators, implantable cardioverters, implantable cardiac pacemakers, implantable defibrillators and cochlear implants. Of course, it is recognized that other implantable medical devices are envisioned which utilize energy delivered or transferred from an external device.

A common element in many of these implantable medical devices is the need for electrical power in the implanted medical device. The implanted medical device may require electrical power to perform its therapeutic function whether it be driving an electrical infusion pump, providing an electrical neurostimulation pulse or providing an electrical cardiac stimulation pulse. This electrical power is derived from a power source.

Typically, a power source for an implantable medical device is a rechargeable power source. In this form, an internal power source, such as a battery, can be used for direct electrical power to the implanted medical device. When the battery has expended, or nearly expended, its capacity, the battery can be recharged transcutaneously, via inductive coupling from an external power source temporarily positioned on the surface of the skin.

The external power source typically may have an external antenna that is placed in the proximity of a corresponding internal antenna associated with the implantable medical device.

In order to charge or recharge the implantable medical device's rechargeable power source, it is typical for the user to place an external charger, or an antenna associated with an external charger, in the proximity of the implantable medical device, or in the proximity of an internal or secondary antenna or coil associated with the implantable medical device. Optimally, the primary coil of the external charger will be aligned as closely as possible with the secondary coil of the implantable medical device minimizing the distance between the two coils and providing a relatively efficient transfer of energy between the external charger and implantable medical device.

SUMMARY

It may sometimes be difficult for the user to exactly locate the external antenna, or more particularly, the primary coil in the proper location with respect to the internal secondary antenna of the implantable medical device for optimal charging or power transfer efficiency. Exact location is complicated by determining the exact proper location. Although a bulge created by the implantable medical device is commonly used to locate the external antenna, the center of the bulge may not be the proper location because the secondary coil associated with the implantable medical device may not be centered with respect to the implantable medical device and, hence, may not be centered with respect to the bulge. Further, it is often difficult to secure the external antenna in the proper location even if the proper location is known. Since charging is not an instantaneous procedure, a mechanism is generally employed to secure the external antenna in a location to conduct transcutaneous energy transfer. The securing mechanism may not precisely locate the external antenna or the external antenna may be subject to movement with respect to the patient as a result of the patient's movements.

If the primary coil of the external antenna is not optimally located with respect to the secondary coil of the implantable medical device, optimal efficiency of energy transfer and, hence, charging of the implantable medical device often is not achieved.

In an embodiment, a plurality of primary coils are utilized to provide a wider effective charging area for the external power source. The use of a plurality of concentric primary coils allows at least one of the primary coils to be energized. In particular, the primary coil that provides the best coupling and/or most efficient transcutaneous transfer of energy will be energized. If the external antenna is not accurately or nearly accurately aligned with the secondary coil, then the smallest concentric primary coil of the external power source may not be aligned with the secondary coil of the implantable medical device. More efficient transcutaneous energy transfer may result if a larger one of the plurality of concentric primary coils is energized for transcutaneous energy transfer. In addition, the availability of multiple, i.e., more than one, primary coils of varying diameters possibly results in greater comfort for the user and/or a greater likelihood of success in charging of the implantable medical device by the user.

In an aspect of the present invention, a plurality of primary coils, concentrically arranged, are utilized in the antenna of the external power source. The external power source may select one of the primary coils, for example, to be used to more efficiently transfer energy to the implantable medical device.

In an embodiment, the present invention provides an external power source for an implantable medical device having therapeutic componentry and a secondary coil operatively coupled to the therapeutic componentry. A plurality of concentric primary charging coils are each capable of transcutaneously inductively energizing the secondary coil when externally placed in proximity of the secondary coil. Drive circuitry selectively couples to each of the plurality of concentric primary coils for energizing a selected one of the plurality of concentric primary coils.

In an embodiment, the selected one of the plurality of concentric primary coils is a single selected one of the plurality of concentric primary coils.

In an embodiment, the selected one of the plurality of concentric primary coils is determined by efficiency of energy transfer.

In an embodiment, the selected one of the plurality of concentric primary coils is determined to be one of the plurality of concentric primary coils providing a greatest efficiency of energy transfer between the selected one of the plurality of concentric primary coils and the secondary coil.

In an embodiment, selection circuitry determines which of the plurality of concentric primary coils is selected to be the selected one of the plurality of concentric primary coils.

In an embodiment, the selection circuitry determines the selected one of the plurality of concentric primary coils based on which of the plurality of concentric primary coils provides a greatest efficiency of energy transfer between the selected one of the plurality of concentric primary coils and the secondary coil.

In an embodiment, the selection circuitry periodically checks an efficiency of energy transfer between each of the plurality of primary coils and the secondary coil.

In an embodiment, each of the plurality of concentric primary coils has an inside diameter and an outside diameter, wherein the secondary coil has an outside diameter and wherein a distance between the outside diameter of one of the plurality of concentric primary coils to the inside diameter of a next larger one of the plurality of concentric primary coils is not greater than the outside diameter of the secondary coil.

In an embodiment, the plurality of concentric primary coils lie in a plane.

In an embodiment, a plane of one of the plurality of concentric primary coils is offset from a plane of another of the plurality of concentric primary coils whereby the plurality of concentric primary coils may more easily form over a bulge created by the implantable medical device than if the plurality of concentric primary coils were planar.

In an embodiment, the implantable medical device further has a rechargeable power source operatively coupled to the secondary coil and wherein the selected one of the plurality of concentric primary coils charges the rechargeable power source.

In an embodiment, the present invention provides a method of energizing a secondary coil of an implantable medical having therapeutic output componentry coupled to the secondary coil. An array of a plurality of concentric primary charging coils is positioned in proximity of the secondary coil, each of the plurality of concentric primary charging coils being capable of transcutaneously inductively energizing the secondary coil. One of the plurality of concentric primary coils is selected to be energized. The selected one of the plurality of concentric primary coils is energized.

In an embodiment, only a single one of the plurality of concentric primary coils is selected.

In an embodiment, selecting is determined, at least in part, by an efficiency of energy transfer between the plurality of concentric primary coils and the secondary coil.

In an embodiment, the one of the plurality of concentric primary coils having a greatest efficiency of energy transfer with the secondary coil is selected.

In an embodiment, one of the plurality of concentric primary coils is periodically reselected.

In an embodiment, one of the plurality of concentric primary coils is reselected at least once every minute.

DRAWINGS

DETAILED DESCRIPTION

In order to achieve effective and efficient energy transfer to an implantable medical device and the effective and efficient charging of a rechargeable power source, such as a battery, a proper alignment of a primary coil associated with an external antenna and an external power source with a secondary coil of an implantable medical device is desired. Unfortunately, it is often difficult to achieve the precise alignment desired to obtain the most effective and, possibly, efficient result. Too often, the primary coil of the external device may not be precisely aligned with the secondary coil of the implantable medical device. When this happens, a less than optimal transcutaneous transfer of energy may result.

In an embodiment, a plurality of primary coils are utilized to provide a wider effective charging area for the external power source. The use of a plurality of concentric primary coils allows at least one of the primary coils to be energized, in particular, the primary coil that provides the best coupling and/or most efficient transcutaneous transfer of energy. If the external antenna is accurately or nearly accurately positioned, i.e., laterally aligned, with the secondary coil, then the secondary coil will be most directly aligned with the smallest of the concentric primary coils and that coil may be energized and utilized for transcutaneous energy transfer. If however, the external antenna is not accurately or nearly accurately aligned with the secondary coil, then the smallest concentric primary coil of the external power source may not be aligned with the secondary coil of the implantable medical device. More efficient transcutaneous energy transfer may result if a larger one of the plurality of concentric primary coils is energized for transcutaneous energy transfer, since a larger primary coil, although not accurately aligned, may still cover, or partially cover, the secondary coil resulting in a more efficient transcutaneous transfer of energy than if the smallest primary coil had been energized, which could be completely misaligned with the secondary coil. In addition, the availability of multiple, i.e., more than one, primary coils of varying diameters gives rise to efficient transcutaneous energy transfer with the antenna of the external power source having a larger range of positions, possibly resulting in greater comfort for the user and/or a greater likelihood of success in charging of the implantable medical device by the user.

Figure 1:
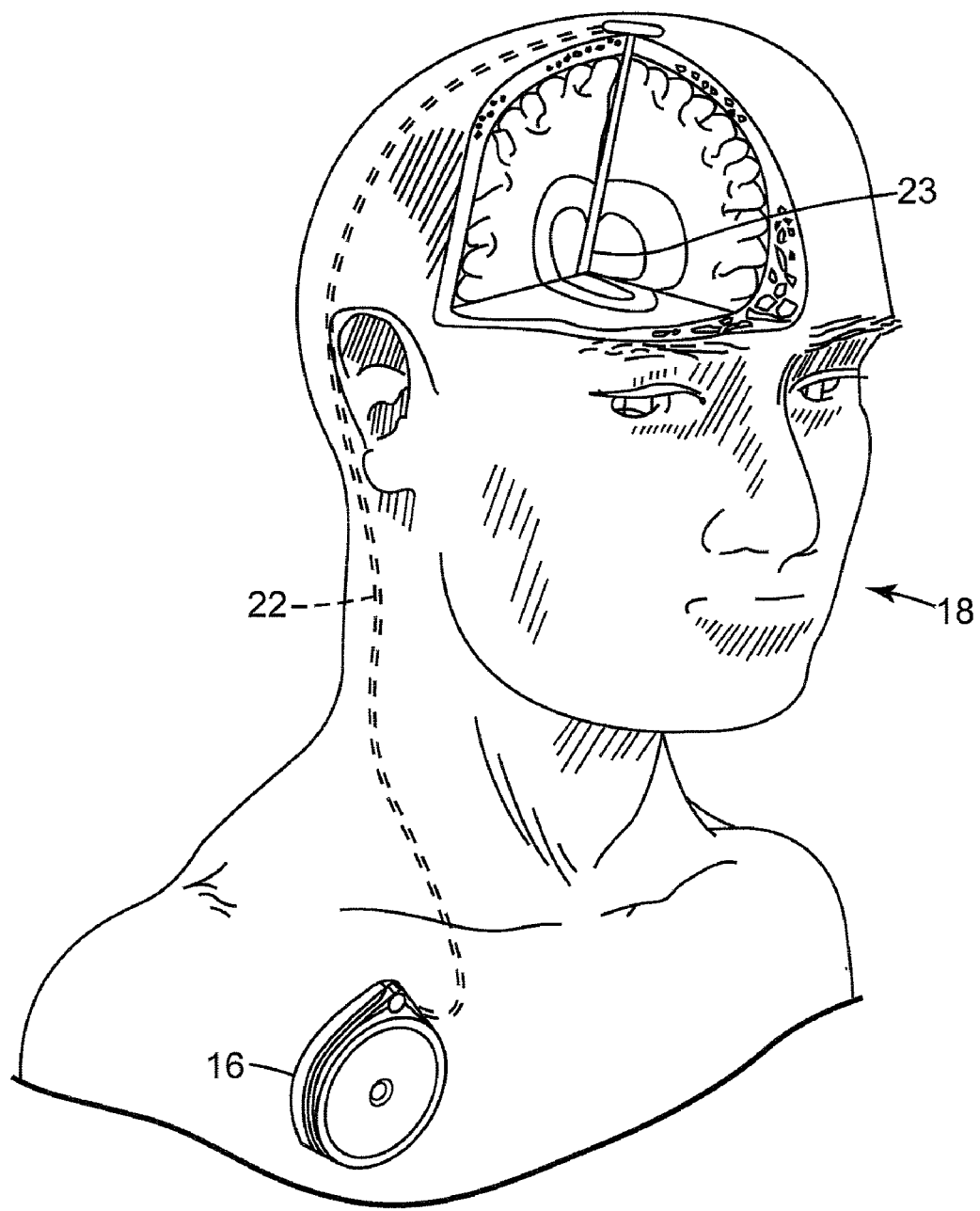
FIG. 1 illustrates an implantable medical device implanted in a patient.

Use of an external power source having an antenna with a plurality of concentric primary coils can generally be illustrated by the generic system in FIG. 1, which shows implantable medical device 16, for example, a neurological stimulator, implanted in patient 18. The implantable medical device 16 is typically implanted by a surgeon in a sterile surgical procedure performed under local, regional, or general anesthesia. Before implanting the medical device 16, a lead 22 is typically implanted with the distal end position at a desired therapeutic delivery site 23 and the proximal end tunneled under the skin to the location where the medical device 16 is to be implanted. Implantable medical device 16 is generally implanted subcutaneously at depths, depending upon application and device 16, of from 1 centimeter (0.4 inches) to 2.5 centimeters (1 inch) where there is sufficient tissue to support the implanted system. Once medical device 16 is implanted into the patient 18, the incision can be sutured closed and medical device 16 can begin operation.

Implantable medical device 16 can be any of a number of medical devices such as an implantable therapeutic substance delivery device, implantable drug pump, electrical stimulator, cardiac pacemaker, cardioverter or defibrillator, as examples.

If implantable medical device 16 is a drug infusion device, for example, implantable medical device 16 operates to infuse a therapeutic substance into patient 18. Implantable medical device 16 can be used for a wide variety of therapies such as pain, spasticity, cancer, and many other medical conditions. The therapeutic substance contained in implantable medical device 16 is a substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances may or may not be intended to have a therapeutic effect and are not easily classified such as saline solution, fluoroscopy agents, disease diagnostic agents and the like. Unless otherwise noted in the following paragraphs, a drug is synonymous with any therapeutic, diagnostic, or other substance that is delivered by the implantable infusion device.

If implantable medical device 16 is an electrical stimulator, as in the embodiment of FIG. 1, therapy module 28 (FIG. 2) may deliver an electrical stimulus, such as an electrical pulse, or series of electrical pulses, either mono-polar or bi-polar, through one or more electrical leads 22 and/or electrodes to provide specific or general benefit to that patient such as pain relief or muscular control.

Figure 2:
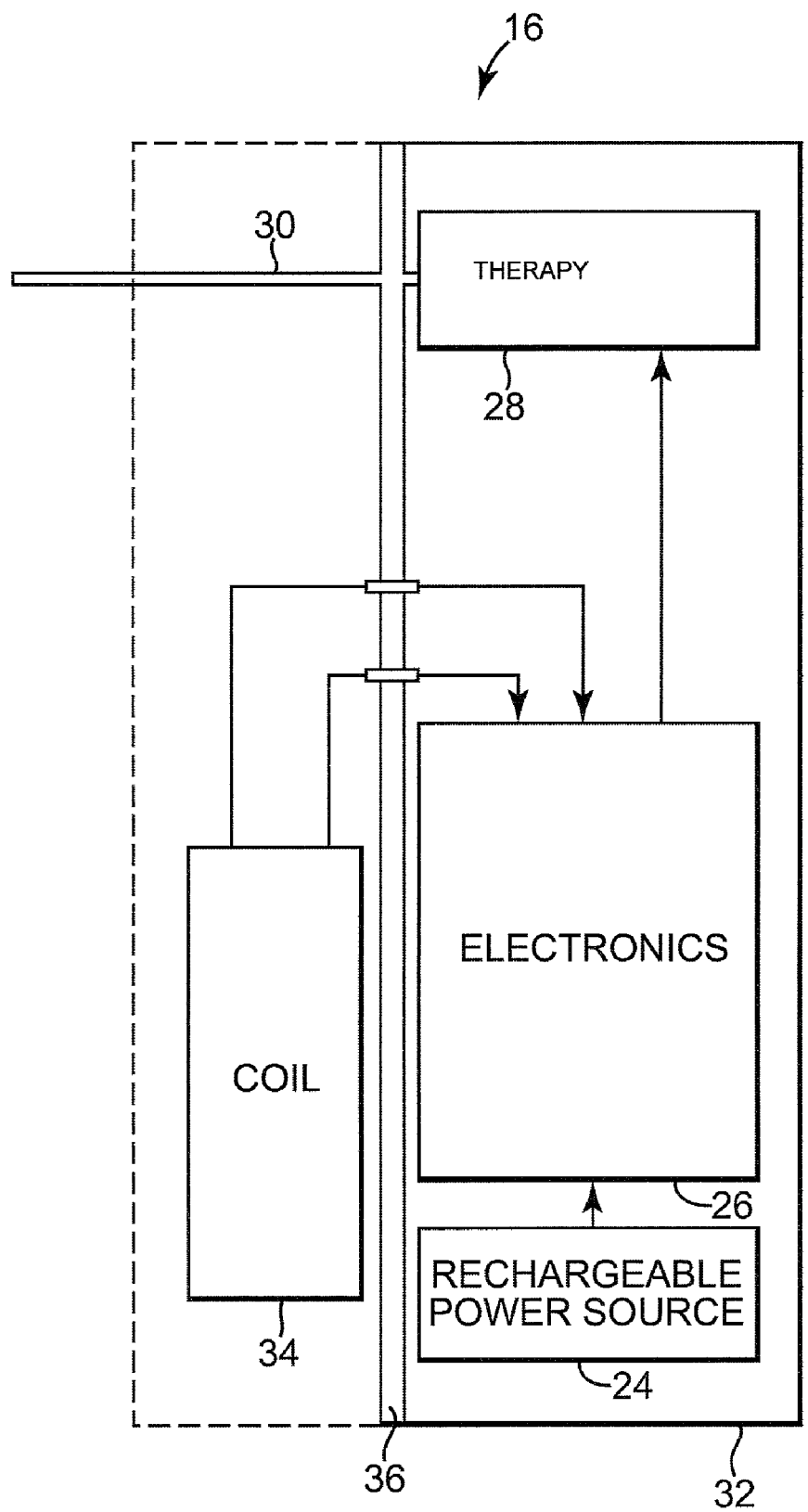
FIG. 2 is a block diagram of an implantable medical device.

In FIG. 2, implantable medical device 16 has a rechargeable power source 24, such as a Lithium ion battery, powering electronics 26 and therapy module 28 in a conventional manner. Therapy module 28 is coupled to patient 18 through one or more therapy connections 30, which is also conventional. Rechargeable power source 24, electronics 26 and therapy module 28 are contained in hermetically sealed housing 32. Secondary charging coil 34 is attached to the exterior of housing 32. Secondary charging coil 34 is operatively coupled through electronics 26 to rechargeable power source 24. In an alternative embodiment, secondary charging coil 34 could be contained in housing 32 or could be contained in a separate housing umbilically connected to electronics 26. Electronics 26 help provide control of the charging rate of rechargeable power source 24 in a conventional manner. Magnetic shield 36 is positioned between secondary charging coil 34 and housing 32 in order to protect rechargeable power source 24, electronics 26 and therapy module 28 from electromagnetic energy when secondary charging coil 34 is utilized to charge rechargeable power source 24.

Rechargeable power source 24 can be any of a variety power sources including a chemically based battery or a capacitor. Rechargeable power source may be a well known lithium ion battery.

Figure 3:
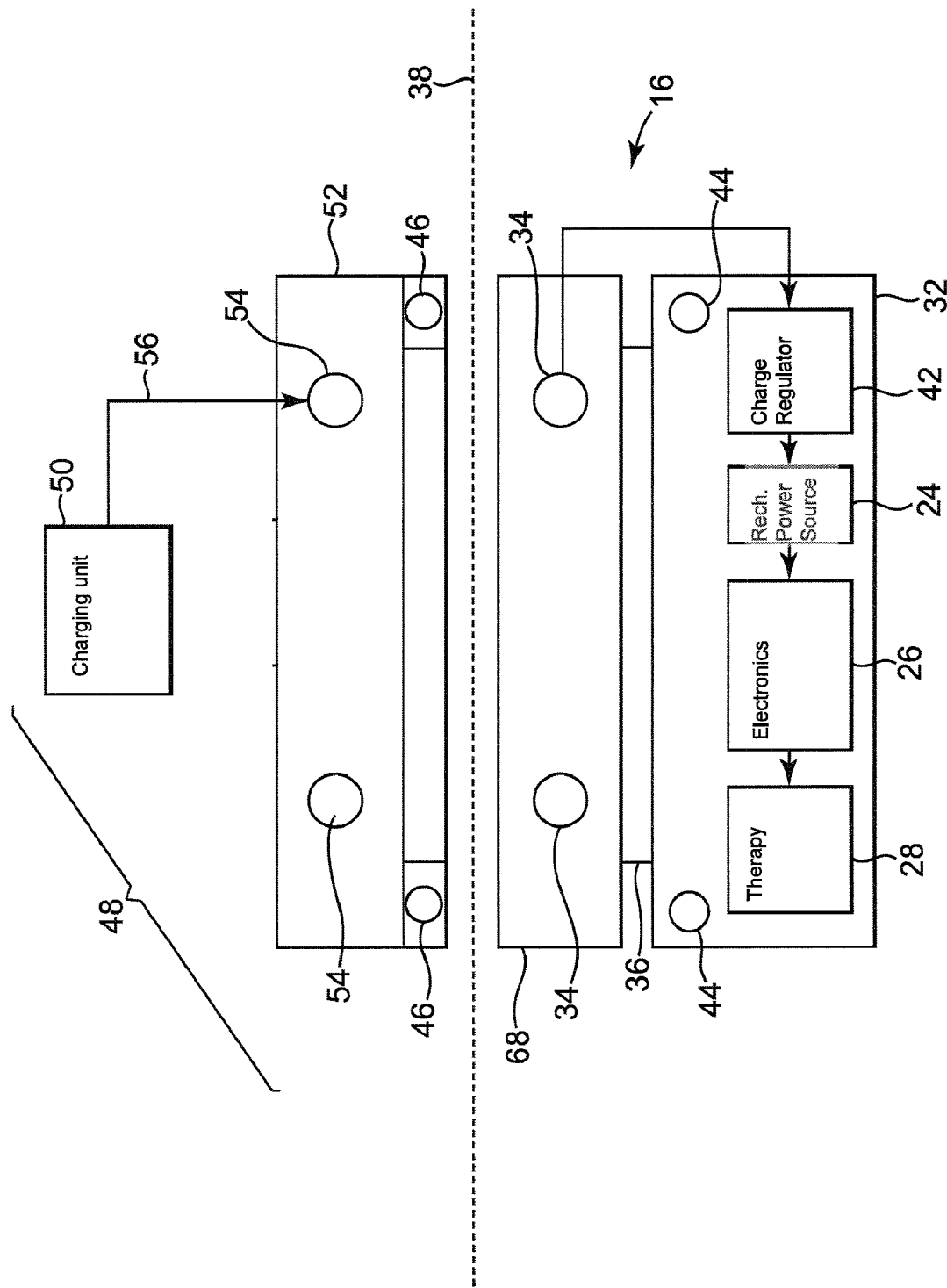
FIG. 3 is a detailed block diagram of an implantable medical device implanted subcutaneously and an associated external power source or charging device.

FIG. 3 illustrates an alternative embodiment of implantable medical device 16 situated under cutaneous boundary 38. Implantable medical device 16 is similar to the embodiment illustrated in FIG. 2. However, charging regulator 42 is shown separate from electronics 26 controlling therapy module 28. Again, charging regulation and therapy control is conventional. Implantable medical device 16 also has internal telemetry coil 44 configured in conventional manner to communicate through external telemetry coil 46 to an external programming device (not shown), charging unit 50 or other device in a conventional manner in order to both program and control implantable medical device 16 and to externally obtain information from implantable medical device 16 once implantable medical device 16 has been implanted. In an embodiment, internal telemetry coil 44 is rectangular in shape with dimensions of 1.85 inches (4.7 centimeters) by 1.89 inches (4.8 centimeters) constructed from 150 turns of 43 AWG wire and is sized to be larger than the diameter of secondary charging coil 34. In this embodiment, secondary coil 34 is located in internal antenna 68 and is constructed with 182 turns of 30 AWG wire with an inside diameter of 0.72 inches (1.83 centimeters) and an outside diameter of 1.43 inches (3.63 centimeters) with a height of 0.075 inches (0.19 centimeters). Magnetic shield 36 is positioned between secondary charging coil 34 and housing 32 and sized to cover the footprint of secondary charging coil 34.

Internal telemetry coil 44, having a larger diameter than secondary coil 34, is not completely covered by magnetic shield 36 allowing implantable medical device 16 to communicate with the external programming device with internal telemetry coil 44 in spite of the presence of magnetic shield 36.

Rechargeable power source 24 can be charged while implantable medical device 16 is in place in a patient through the use of external charging device 48. In an embodiment, external charging device 48 consists of charging unit 50 and external antenna 52. For purposes of illustration in FIG. 3, external charging device or external power source 48 is illustrated with single primary coil 54. More specific illustrations of external antenna 52 with a plurality of concentric primary coils will be illustrated more specifically in later Figures. Charging unit 50 contains the electronics necessary to drive primary coil 54 with an oscillating current in order to induce current in secondary coil 34 when primary coil 54 is placed in the proximity of secondary coil 34. Charging unit 50 is operatively coupled to primary coil by cable 56. In an alternative embodiment, charging unit 50 and antenna 52 may be combined into a single unit. Antenna 52 may also optionally contain external telemetry coil 46 which may be operatively coupled to charging unit 50 if it is desired to communicate to, or from, implantable medical device 16 with external charging device 48. Alternatively, antenna 52 may optionally contain external telemetry coil 46 which can be operatively coupled to an external programming device, either individually or together with external charging unit 48.

Figure 4:
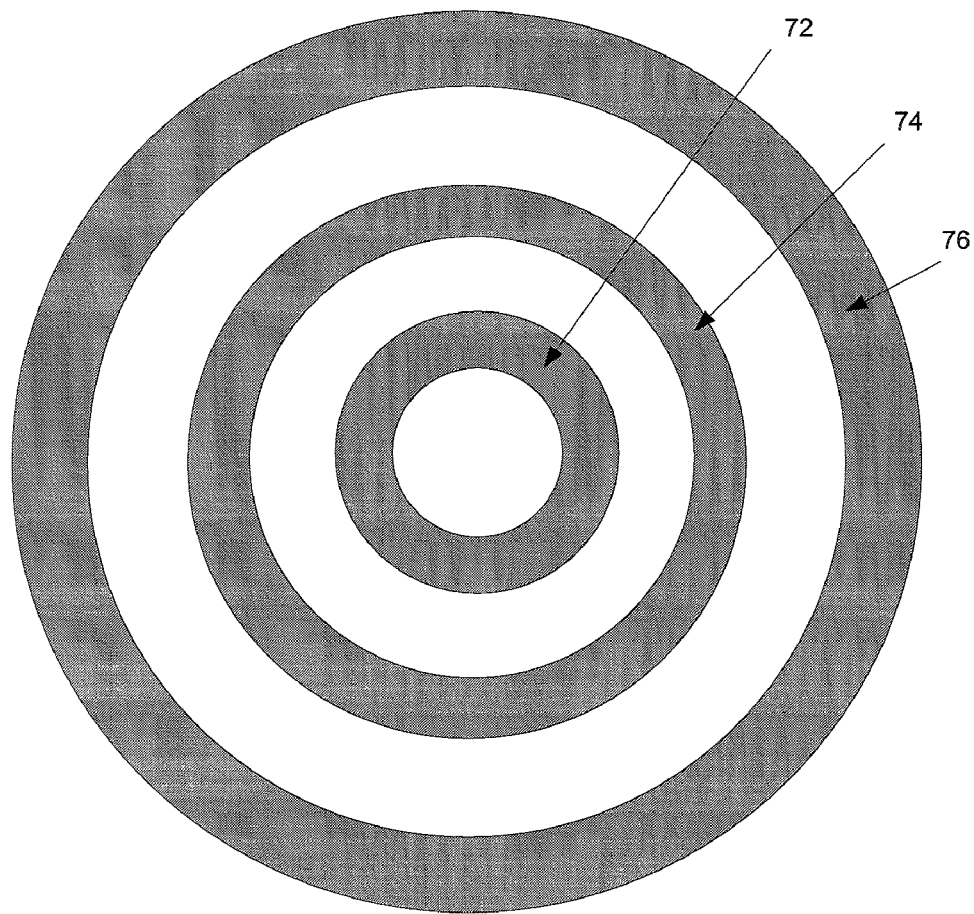
FIG. 4 illustrates a top view of an embodiment of the primary coil arrangement of an external antenna associated with an external power source.

FIG. 4 illustrates a more specific embodiment of primary coil 54 utilized in external antenna 52. Instead of a single primary coil 54 as illustrated in FIG. 3, an embodiment utilizes a plurality of concentric primary coils 72, 74 and 76. Since primary coils 72, 74 and 76 are concentric, each of primary coils 72, 74 and 76 having different diameters. In particular, primary coil 72 is the smallest and is approximately equal in diameter to primary coil 54 illustrated in FIG.

3. Primary coil 74 has a larger diameter than primary coil 72. In effect, primary coil 72 nests inside of primary coil 74. Likewise, primary coil 76 has a larger diameter than primary coil 74. Primary coil 72 and primary coil 74 nest inside of primary coil 76.

In an embodiment, primary coils 72, 74, 76 are constructed from 100 to 150 turns of 40 AWG wire. Primary coils 72, 74, 76 may be driven between 30 and 50 kiloHertz. In an embodiment, primary coil 76 has an outside diameter of approximately six-and-a-half inches (16.5 centimeters) and an inside diameter of approximately five-and-a-half inches (14.0 centimeters), primary coil 74 has an outside diameter of approximately four-and-a-half inches (11.4 centimeters) and an inside diameter of approximately three-and-a-half inches (8.9 centimeters), and primary coil 72 has an outside diameter of approximately two-and-a-half inches (6.35 centimeters) and an inside diameter of approximately one-and-a-quarter inches (3.2 centimeters). However, alternative diameters for primary coils 72, 74, 76 are envisioned depending on a variety of factors, such as the dimensions of implantable medical device 16 and physical characteristics of patient 18 that may be conducive to relatively larger or smaller primary coils 72, 74, 76.

Figure 5:
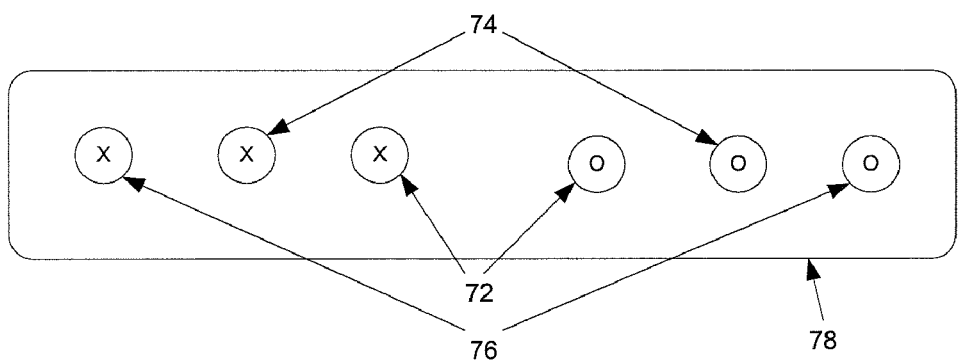
FIG. 5 illustrates a side cross-sectional view of the embodiment of the primary coil arrangement of an external antenna associated with an external power source illustrated in FIG. 4.

FIG. 5 illustrates a cross-sectional view of the embodiment of primary coil 54 shown in FIG. 4. Antenna housing 78 contains primary coil 72 nested inside of primary coil 74, and both primary coil 72 and primary coil 74 are nested inside of primary coil 76. As depicted, in an embodiment primary coil 72, primary coil 74 and primary coil 76 are on substantially the same plane. In this embodiment, antenna housing 78 is made of a substantially inflexible plastic or similar material known in the art and, thus, is substantially rigid. Primary coil 72, primary coil 74 and primary coil 76 are largely fixed within antenna housing 78 and are not enabled to shift relative to each other, with each primary coil 72, 74, 76 maintaining the same position relative to each other coil and antenna housing 78.

Figure 6:
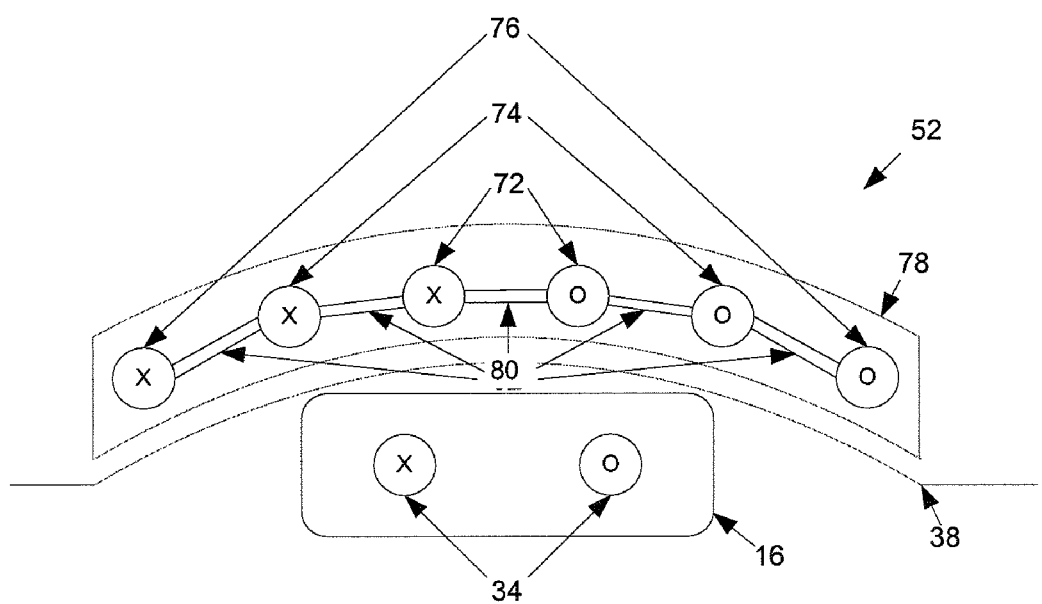
FIG. 6 illustrates a side cross-sectional view of another embodiment of the primary coil arrangement of an external antenna associated with an external power source illustrated in FIG. 4.

FIG. 6 illustrates a cross-sectional view of an embodiment in which antenna housing 78 is pliable and flexible, and primary coils 72, 74 and 76 may shift with respect to each other. Rather than being comprised of a rigid material, antenna housing 78 is made from a substantially flexible material such as fabric or nylon. Primary coil 72, primary coil 74 and primary coil 76 are not fixed in relation to each other, though primary coil 72 is connected to primary coil 74, and primary coil 74 is connected to primary coil 76, by flexible couplers 80, allowing primary coils 72, 74 and 76 to shift with respect to each other, but to maintain proximity with each other, and maintain approximately the same distance between each primary coil 72, 74, 76. In an embodiment, flexible couplers 80 may be comprised of an insulating material to prevent shorting one primary coil 72, 74, 76 with another. Conductive materials, such as metal wires, may be included in flexible couplers 80 to operatively couple charging unit 50 to an intended destination primary coil 72, 74 and 76. However, insulating materials may still be used to prevent conductive materials from coming into contact with any other than the intended destination primary coil 72, 74, 76.

In an embodiment, the distance between the outside diameter of primary coil 72, 74 to the inside diameter of primary coil 74, 76, respectively, is not greater than the outside diameter of secondary coil 34.

This embodiment allows external antenna 52 to form a cup-like shape, conforming to the bulge created in cutaneous boundary 38 by implantable medical device 16. As can be seen in FIG. 6, the creation of a cup-like shape may bring one or more of primary coil 72, 74, 76 into closer proximity of secondary coil 34, thereby potentially creating a more effective and efficient energy transfer than would naturally be attainable if antenna housing 78 were rigid. Advantageously, this embodiment creates an external antenna 52 that offers increased patient comfort, due to its ability to conform to the contours of the patient's body. In an embodiment, patient comfort may be enhanced, while the heating of tissue at cutaneous boundary 38 may be reduced, by making antenna housing 78 of a porous or breathable material, or by omitting antenna housing 78 material in some places between primary coils 72, 74, 76.

Figure 7:
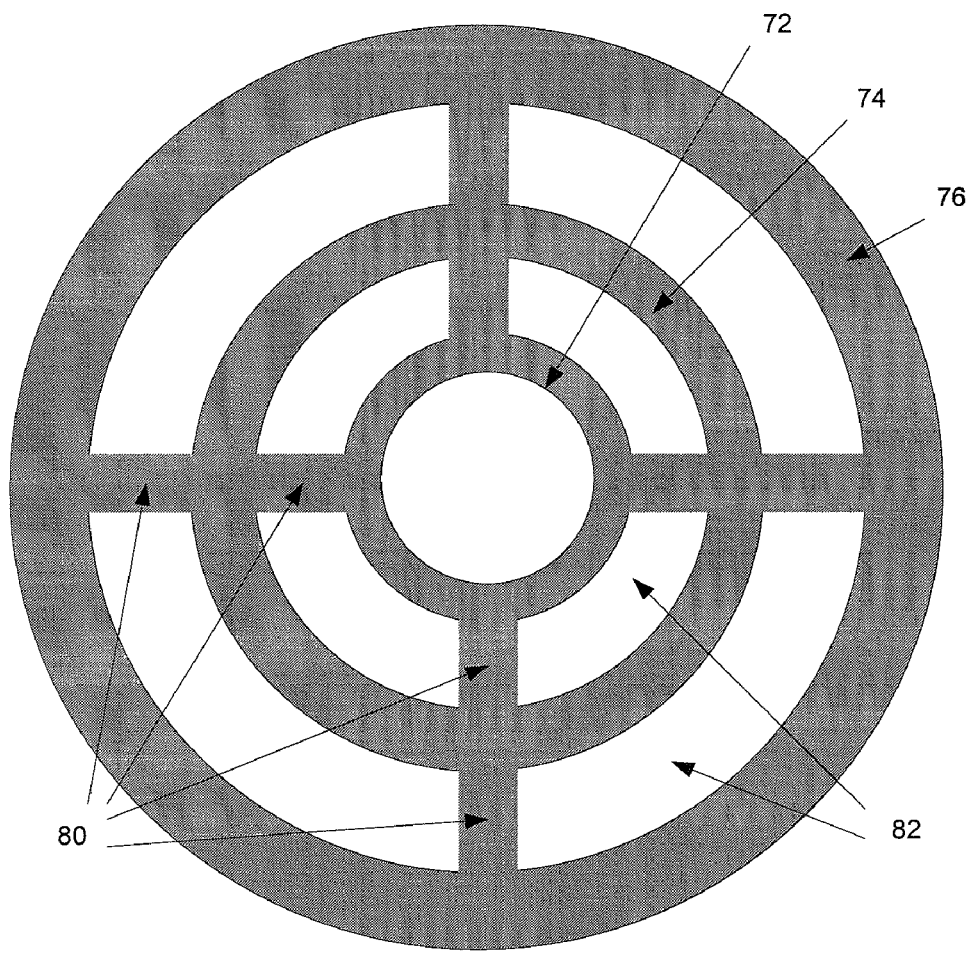
FIG. 7 illustrates a top view of another embodiment of the primary coil arrangement of an external antenna associated with an external power source.

FIG. 7 illustrates a top view of the flexible external antenna 52 depicted in FIG. 6. Primary coils 72, 74 and 76 remain concentric relative to each other, with primary coil 72 connected to primary coil 74, and primary coil 74 connected to primary coil 76, via flexible couplers 80. In an embodiment, void areas 82 may be left free of antenna housing 78 material, or antenna housing 78 material in void areas 82 may be comprised of porous or breathable material, such as nylon mesh.

Figure 8:
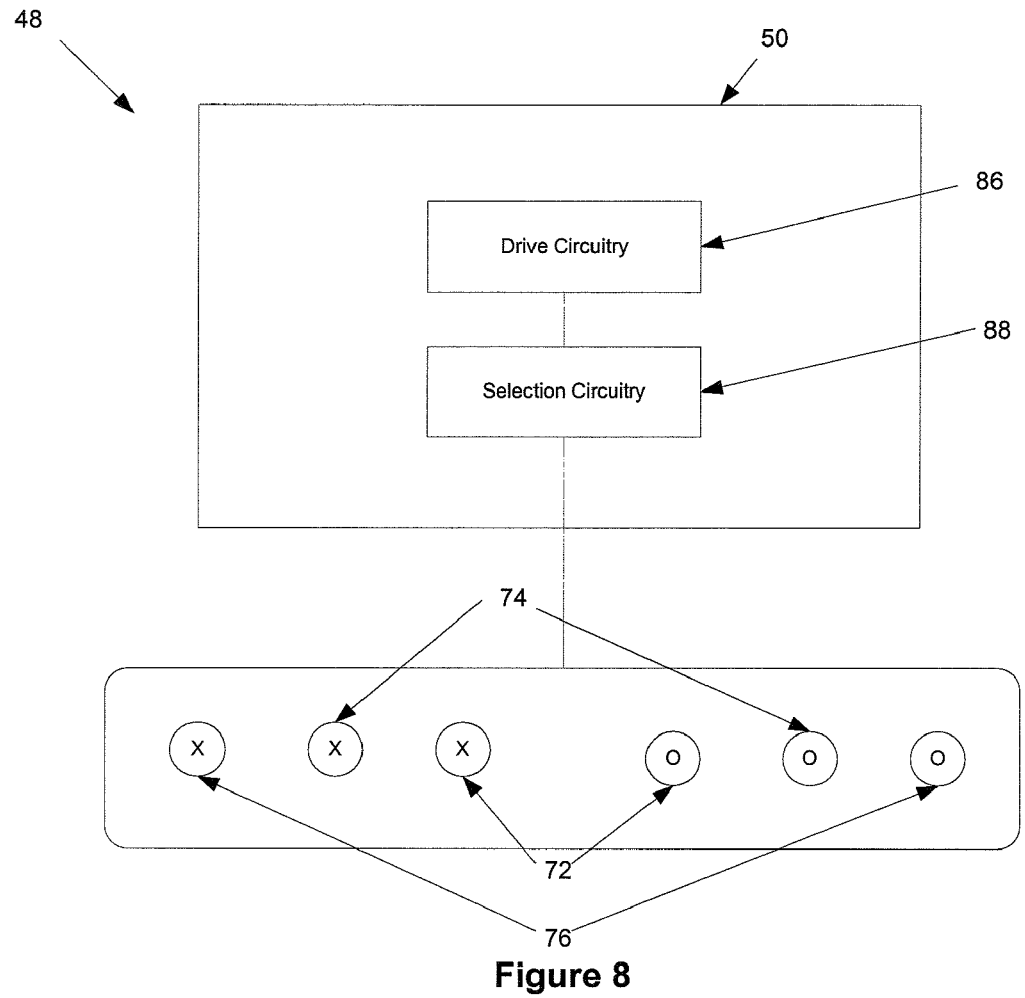
FIG. 8 is a block diagram schematic representation of an external power source including an external antenna.

FIG. 8 shows a block diagram of an embodiment of external charger 48. Charging unit 50 includes drive circuitry 86 that drives primary coils 72, 74, 76 with an oscillating current. Charging unit 50 further includes selection circuitry 88 that determines which primary coil 72, 74, 76 drive circuitry 88 will drive. Selection circuitry 88 may be comprised of standard, off-the-shelf componentry, including a processor and memory units. Alternatively, selection circuitry 88 may be comprised of other standard components known in the art, such as comparators. Selection circuitry 88 further comprises a switch, which may variably conduct the oscillating current generated by drive circuitry 86 to the intended destination primary coil 72, 74, 76.

Figure 9:
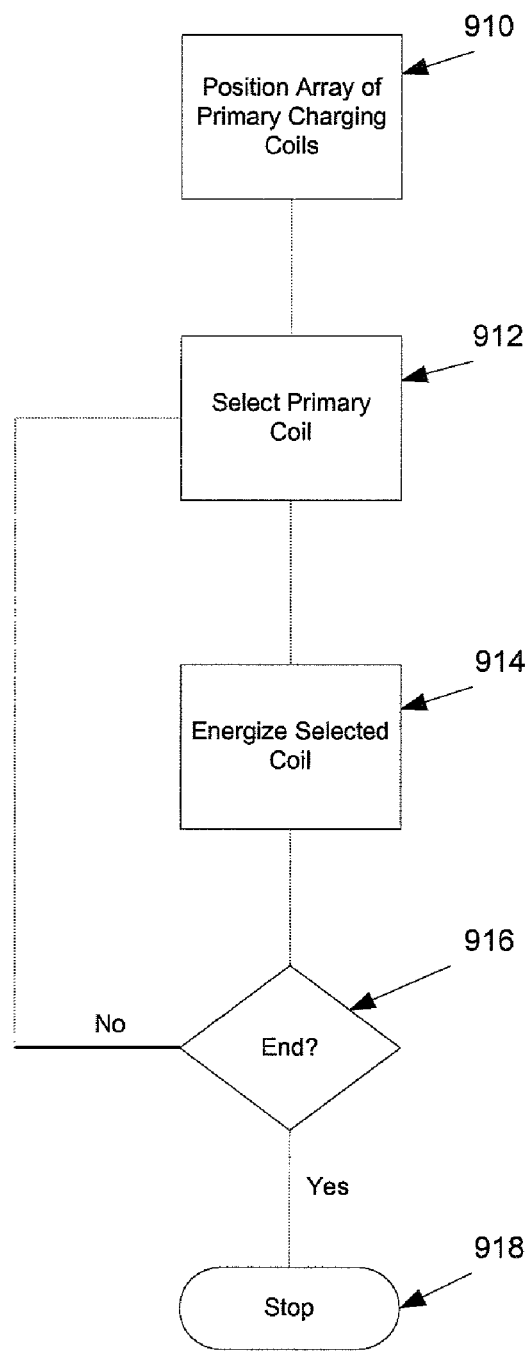
FIG. 9 is a flow chart illustrating a method of energizing a secondary coil of the implantable medical device using an external antenna having plurality of primary coils.

An embodiment of a recharge session is described in FIG. 9. When a user elects to conduct a charging session, external antenna 52 is positioned (910) relative to implantable medical device 16 such that primary coils 72, 74, 76 are in proximity of secondary coil 34, and external telemetry coil 46 is in proximity of internal telemetry coil 44. Selection circuitry 88 selects (912) a primary coil 72, 74, 76 (which process is described in FIG. 10), and drive circuitry 86 energizes (914) selected primary coil 72, 74, 76. After selected primary coil 72, 74, 76 has been energized for some period of time, in an embodiment one minute, it is determined whether the recharging session should end (916). If not, selection circuitry 88 again selects (912) a primary coil 72, 74, 76, and drive circuitry 86 energizes (914) the selected primary coil 72, 74, 76. This process is repeated until it is determined that the process should end, at which point recharging is stopped (918).

Figure 10:
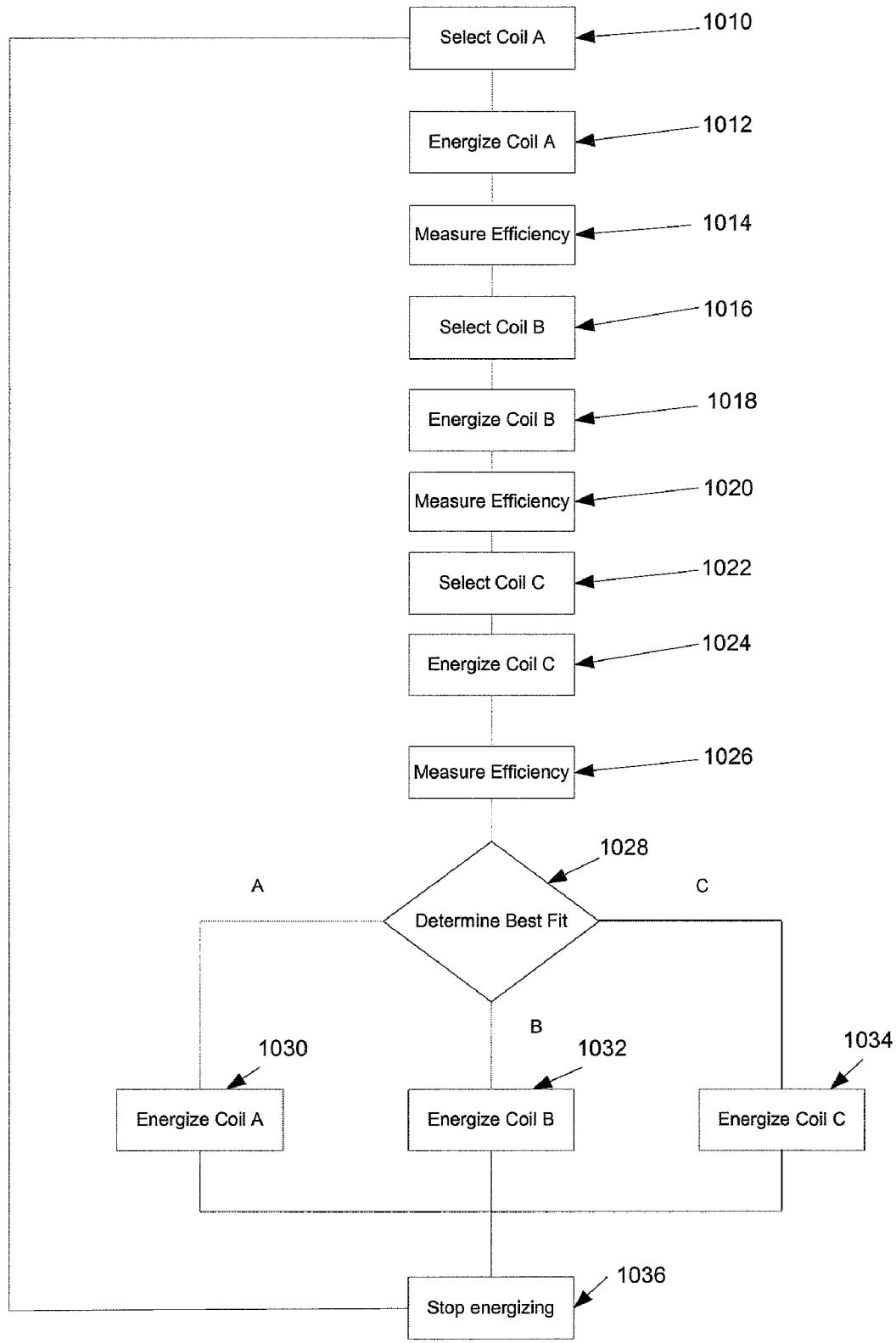
FIG. 10 is a flow chart illustrating in more detail a method of energizing a secondary coil of the implantable medical device using an external antenna having plurality of primary coils.

In an embodiment described in FIG. 10, when external telemetry coil 46 is in proximity of internal telemetry coil 44, selection circuitry 88 initially selects (1010) one primary coil 72, and energizes (1012) primary coil 72. Selection circuitry 88 then measures (1014) and records the efficiency of the connection between primary coil 72 and secondary coil 34 by comparing the power delivered to primary coil 72 and the power generated in secondary coil 34, as reported to external charging device 48 via internal telemetry coil 44 and external telemetry coil 46. Selection circuitry 88 then selects (1016) and energizes (1018) primary coil 74, and again measures (1020) and records the efficiency of the connection between primary coil 74 and secondary coil 34. The efficiency may be reported to external charging device, or another external device, in the manner discussed above. Selection circuitry 88 then selects (1022) and energizes (1024) primary coil 76, and again measures (1026) and records the efficiency of the connection between primary coil 76 and secondary coil 34 and reports the efficiency in the above-described manner. In embodiments with other than three primary coils 72, 74, 76, this procedure may be expanded or contracted to correspond to the number of primary coils 72, 74, 76, such that the efficiency of the connection between each primary coil 72, 74, 76 and the secondary coil is measured and recorded. In another embodiment, the efficiencies of the various primary coils may be recorded within an internal storage device of implantable medical device 16 and transferred to external charging device 48 all at once after all measurements have been completed.

After the efficiency between each primary coil 72, 74, 76 and secondary coil 34 has been measured and recorded, selection circuitry 88 determines (1028) which primary coil 72, 74, 76 has the best, most efficient connection with secondary coil 34. Where primary coil 72 has the most efficient connection, primary coil 72 is energized (1030). Where primary coil 74 has the most efficient connection, primary coil 74 is energized (1032). Where primary coil 76 has the most efficient connection, primary coil 76 is energized (1034). The selected coil may remain energized until a period of time has elapsed, in an embodiment one minute, at which point energizing stops (1036), and the process begins again by selecting (1010) primary coil 72. The process may repeat until the recharge session has been completed (FIG. 9).

In an embodiment, a plurality of primary coils 72, 74, 76, for example two of primary coils 72, 74, 76, could be energized simultaneously. In secondary coil 34 is not exactly aligned with one of primary coils 72, 74, 76 but rather is aligned, for example, between primary coils 74 and 76, then it may be desirable to energize both of primary coils 74 and 76 than having to choose only one of primary coils 72, 74, 76.

Thus, embodiments of concentric primary coils for inductively charging an implantable medical device, external power source and method are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An external power source for an implantable medical device, said implantable medical device having therapeutic componentry and a secondary coil operatively coupled to said therapeutic componentry, said external power source comprising:
a plurality of co-axial primary charging coils, each individual one of said plurality of co-axial primary charging coils having a major plane and being capable of transcutaneously inductively energizing said secondary coil when externally placed in proximity of said secondary coil, said major plane of each of said plurality of primary charging coils being parallel and co-planar with said major plane of each other of said plurality of primary charging coils; and
drive circuitry selectively coupled to each of said plurality of co-axial primary coils for energizing a selected one of said plurality of co-axial primary coils.

2. The external power source as in claim 1 wherein said selected one of said plurality of co-axial primary coils is a single selected one of said plurality of co-axial primary coils.

3. The external power source as in claim 1 wherein said selected one of said plurality of co-axial primary coils is determined by efficiency of energy transfer.

4. The external power source as in claim 3 wherein said selected one of said plurality of co-axial primary coils is determined to be one of said plurality of co-axial primary coils providing a greatest efficiency of energy transfer between said selected one of said plurality of co-axial primary coils and said secondary coil.

5. The external power source as in claim 1 further comprising selection circuitry operatively coupled to drive circuitry, said selection circuitry determining which of said plurality of co-axial primary coils is selected to be said selected one of said plurality of co-axial primary coils.

6. The external power source as in claim 5 wherein said selection circuitry determines said selected one of said plurality of co-axial primary coils based on which of said plurality of co-axial primary coils provides a greatest efficiency of energy transfer between said selected one of said plurality of co-axial primary coils and said secondary coil.

7. The external power source as in claim 6 wherein said selection circuitry periodically determines an efficiency of energy transfer between each of said plurality of primary coils and said secondary coil.

8. The external power source as in claim 1 wherein each of said plurality of co-axial primary coils has a primary coil major axis, an inside diameter with respect to said primary coil major axis and an outside diameter with respect to said primary coil major axis, wherein said secondary coil has a secondary coil major axis and an outside diameter with respect to said secondary coil major axis and wherein a distance between said outside diameter of one of said plurality of co-axial primary coils to said inside diameter of a next larger one of said plurality of co-axial primary coils is not greater than said outside diameter of said secondary coil.

9. The external power source as in claim 1 wherein said implantable medical device further has a rechargeable power source operatively coupled to said secondary coil and wherein said selected one of said plurality of co-axial primary coils charges said rechargeable power source.

10. A method of energizing a secondary coil of an implantable medical having therapeutic output componentry coupled to said secondary coil, comprising the steps of:
positioning an array of a plurality of co-axial primary charging coils in proximity of said secondary coil, each of said plurality of co-axial primary charging coils having a major plane and being capable of transcutaneously inductively energizing said secondary coil, said major plane of each of said plurality of primary charging coils being parallel and co-planar with said major plane of each other of said plurality of primary charging coils;
selecting a selected one of said plurality of co-axial primary coils to be energized; and
energizing said selected one of said plurality of co-axial primary coils.

11. The method as in claim 10 wherein said selecting step selects only a single one of said plurality of co-axial primary coils.

12. The method as in claim 10 wherein said selecting step is determined, at least in part, by an efficiency of energy transfer between said plurality of co-axial primary coils and said secondary coil.

13. The method as in claim 12 wherein said selecting step selects one of said plurality of co-axial primary coils having a greatest efficiency of energy transfer with said secondary coil.

14. The method as in claim 13 wherein said selecting step periodically reselects one of said plurality of co-axial primary coils.

15. The method as in claim 14 wherein said selecting step reselects one of said plurality of co-axial primary coils at least once every minute.

* * * * *